US009839660B2

(12) United States Patent
Park et al.

(10) Patent No.: US 9,839,660 B2
(45) Date of Patent: Dec. 12, 2017

(54) **METABOLISM ACCELERATING COMPOSITION COMPRISING *ASTRAGALI RADIX* EXTRACT**

(75) Inventors: Pil Joon Park, Yongin-si (KR); Si Young Cho, Seoul (KR); Dae Bang Seo, Yongin-si (KR); Sang Jun Lee, Seongnam-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 235 days.

(21) Appl. No.: 13/512,800

(22) PCT Filed: Nov. 29, 2010

(86) PCT No.: PCT/KR2010/008488
§ 371 (c)(1),
(2), (4) Date: May 30, 2012

(87) PCT Pub. No.: WO2011/065791
PCT Pub. Date: Jun. 3, 2011

(65) Prior Publication Data
US 2012/0237625 A1  Sep. 20, 2012

(30) Foreign Application Priority Data
Nov. 30, 2009  (KR) ........................ 10-2009-0116640

(51) Int. Cl.
*A61K 36/00* (2006.01)
*A61K 36/481* (2006.01)
*A23L 33/105* (2016.01)

(52) U.S. Cl.
CPC .......... *A61K 36/481* (2013.01); *A23L 33/105* (2016.08); *A23V 2002/00* (2013.01)

(58) Field of Classification Search
None
See application file for complete search history.

(56) References Cited

U.S. PATENT DOCUMENTS 6,193,973 B1 * 2/2001 Tuttle ............................ 424/728
2007/0053999 A1   3/2007 Wei et al.

FOREIGN PATENT DOCUMENTS

| CN | 1481806 A | * | 3/2004 |
| CN | 1557403 A | * | 12/2004 |
| CN | 1582984 A | * | 2/2005 |
| CN | 1850185 A | * | 10/2006 |
| CN | 100998715 A | * | 7/2007 |
| JP | 7-278012 A | | 10/1995 |
| JP | 2008-538118 A | | 10/2008 |
| JP | 2009107945 A | * | 5/2009 |
| KR | 10-0195884 B1 | | 6/1999 |
| KR | 2000-0037056 A | | 7/2000 |
| KR | 10-0284657 B1 | | 4/2001 |
| KR | 10-2006-0057291 A | | 5/2006 |
| KR | 10-2009-0073462 A | | 7/2009 |

OTHER PUBLICATIONS

Li, The Effect of Radix Astragali on the Swimming Endurance of Mice and Its Relation With the Gonads. Journal of China Medical University, (1986) vol. 15, No. 3, pp. 173-175.*
Gao et al, Protective effect of radix astragali on soleus muscle. Chinese Journal of Clinical Rehabilitation, (Jun. 20, 2006) vol. 10, No. 23, pp. 54-56.*
Caron et al, A novel hindlimb immobilization procedure for studying skeletal muscle atrophy and recovery in mouse. Journal of Applied Physiology (2009), 106(6), 2049-2059.*
J.H. Cho et al., "Myelophil, an Extract Mix of Astragali Radix and Salviae Radix, Ameliorates Chronic Fatigue: A Randomised, Double-Blind, Controlled Pilot Study," Complementary Therapies in Medicine, vol. 17, pp. 141-146, 2009.
Y. Shon et al., Protective Effect of Astragali Radix Extract on Interleukin 1β-induced Inflammation in Human Amnion, Phytotherapy Research, vol. 17, pp. 1016-1020, 2003.
N. Baek et al., "Isolation of Anti-Hepatotoxic Agent from the Root of Astragalus Membranaceus," Korean Journal of Pharmacognosy, vol. 27, No. 2, pp. 111-116, 1996.
H. Kang et al., "Immuno Modulatory Effect of Astragali Radix on OVA Induced Allergic Mouse Model," Korean Journal of Oriental Physiology and Pathology, vol. 19, No. 3, pp. 612-617, 2005.
P. Puigserver et al., "Peroxisome Proliferator-Activated Receptor-γ Coactivator 1α (PGC-1α): Transcriptional Coactivator and Metabolic Regulator," Endocrine Reviews, vol. 24, No. 1, pp. 78-90, 2003.
Li Shenwen, et al., "The Effect of Radix Astragali on Swimming Endurance of Mice and Its Relation with the Gonads." Neuroendocrine Laboratory, Journal of China Medical University, vol. 15, No. 3, pp. 173-175, 1986.
Liu Kemin, et al., "Modern Journal of Integrated Traditional Chinese and Western Medicine." vol. 17, No. 14, pp. 2346-2347 and 2349, Sep. 2005.

* cited by examiner

*Primary Examiner* — Qiuwen Mi
(74) *Attorney, Agent, or Firm* — Blank Rome LLP

(57) ABSTRACT

The present invention provides a composition comprising *Astragali Radix* extract as an active ingredient. The composition can increase body energy consumption and muscle metabolism. The present invention also relates to pharmaceutical and food compositions which include a composition comprising the *Astragali Radix* extract. The pharmaceutical and food compositions also increase body energy consumption and muscle metabolism.

4 Claims, 1 Drawing Sheet

【Figure 1】
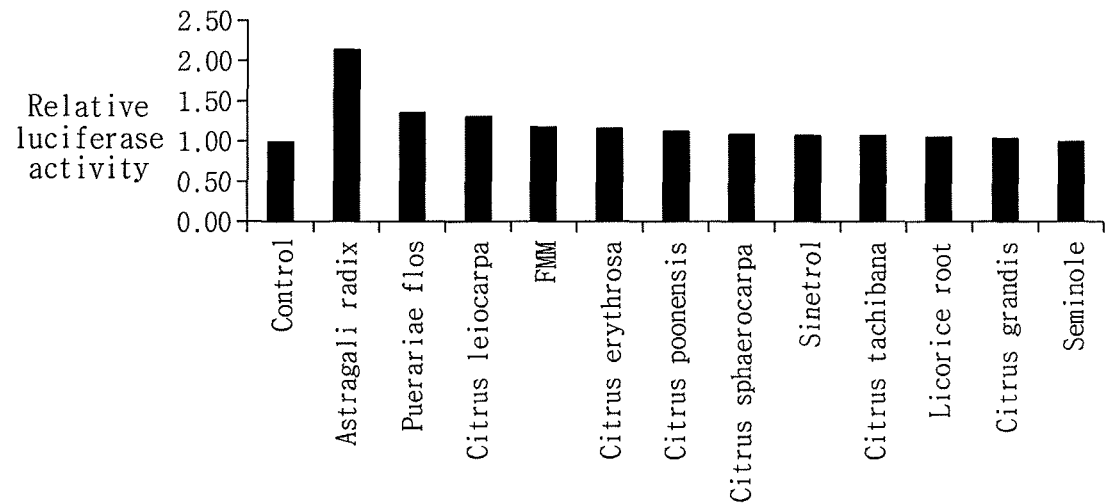
【Figure 2】
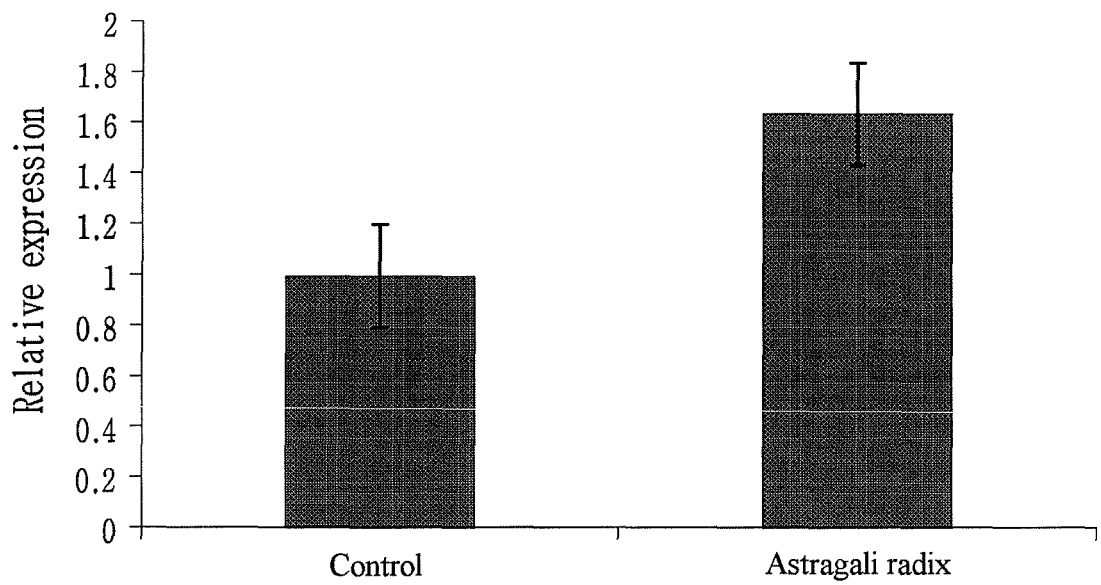

METABOLISM ACCELERATING COMPOSITION COMPRISING *ASTRAGALI RADIX* EXTRACT

TECHNICAL FIELD

The present disclosure relates to a composition comprising *astragali radix* extract as an active ingredient.

BACKGROUND ART

All organisms absorb necessary substances from their surroundings. They synthesize necessary substances using the absorbed substances and also break them down to obtain required energy. They also excrete byproducts or wastes produced during the process. All these processes required by the organisms for maintenance of life are called metabolism.

Metabolism is usually divided into anabolism and catabolism. Anabolism is a process of synthesizing high-molecular-weight compounds from low-molecular-weight organic or inorganic matters absorbed from the surroundings. Typical examples of anabolism are photosynthesis and protein synthesis. In anabolism, light or chemical energy is required. Catabolism is the reverse process of breaking down high-molecular-weight compounds into low-molecular-weight organic or inorganic matters. Examples of catabolism include cellular respiration and digestion. Through catabolism, organisms acquire the energy necessary for activities. In general, anabolism is accompanied by an energy-absorbing endothermic reaction and catabolism is accompanied by an energy-releasing exothermic reaction. Accordingly, metabolism of substance is accompanied by an energy metabolism.

DISCLOSURE

Technical Problem

The inventors of the present disclosure have found out that *astragali radix* extract promotes energy consumption and muscular metabolism. Thus, the present disclosure is directed to providing a composition for promoting energy consumption and muscular metabolism comprising *astragali radix* extract as an active ingredient.

Technical Solution

In one general aspect, the present disclosure provides a composition for promoting energy consumption, promoting muscular metabolism, enhancing stamina, strengthening muscles or relieving muscular pain comprising *astragali radix* extract as an active ingredient.

In another general aspect, the present disclosure provides pharmaceutical and food compositions comprising the *astragali radix* extract as an active ingredient.

Advantageous Effects

The composition according to the present disclosure which comprises *astragali radix* extract as an active ingredient has an effect of promoting energy consumption and muscular metabolism by promoting expression of peroxisome proliferator-activated receptor gamma coactivator 1-alpha (PGC1-α) and promoting production of mitochondria. Accordingly, it may provide the effect of increasing basal metabolic rate, reducing muscular damage, enhancing stamina, strengthening muscles, relieving muscular pain, and so forth. Also, a pharmaceutical composition and a food composition comprising the composition may have the effect of promoting energy consumption and muscular metabolism and thus the effect of increasing basal metabolic rate, reducing muscular damage, enhancing stamina, strengthening muscles, relieving muscular pain, and so forth.

DESCRIPTION OF DRAWINGS

FIG. 1 is a graph which depicts expression level of luciferase resulting from activation of promoter of PGC1-α by *astragali radix* extract and other substances.

FIG. 2 is a graph which compares expression level of PGC1-α in muscle cells treated with *astragali radix* extract with that of a negative control group.

BEST MODE

As used herein, the term "extract" includes any substance extracted from a natural product, regardless of the types of substance. It includes, for example, an extract extracted from a natural product using a solvent such as water or an organic solvent, or a specific substance extracted from the natural product such as oil.

As used herein, the term "metabolism" refers to a process occurring in an organism whereby nutrients ingested from outside are broken down in the body, substances or energy necessary to maintain structures or activities are produced, and unnecessary substances are excreted out of the body. If the metabolism occurs actively, energy consumption of the body increases.

The present disclosure is described in detail hereunder.

Mitochondria regulate fatty acid oxidation. As a result of fatty acid oxidation by mitochondria, energy is stored as ATP. The number and ability of the mitochondria that regulate the fatty acid oxidation are known to be regulated by peroxisome proliferator-activated receptor gamma coactivator 1-alpha (PGC1-α). Also, it has been found out in PGC1-α-deficient knockout mice that PGC1-α is essential in production of mitochondria. In addition, it is known that genes involved in mitochondrial production decrease remarkably in all tissues of a PGC1-α-deficient knockout mouse, including skeletal muscles, brain, adipose tissue and liver. As a result, the main function of oxidative metabolism by mitochondria is lost in all the tissues and the mouse gains weight as it loses motility. Accordingly, it can be concluded that PGC1-α is involved in regulation of metabolism in tissues.

Thus, a substance that promotes expression of PGC1-α can promote the production of mitochondria, which in turn promotes fatty acid oxidation by mitochondria and promotes energy consumption by producing ATP. Especially, a substance that promotes expression of PGC1-α in muscle cells will be able to promote muscular metabolism.

Such a substance can promote energy consumption and muscular metabolism. The promotion of muscular metabolism may provide the effect of increasing basal metabolic rate, reducing muscular damage, enhancing stamina, strengthening muscles, and relieving muscular pain.

The present disclosure provides a composition for promoting energy consumption and muscular metabolism, comprising *astragali radix* extract as an active ingredient.

*Astragali radix* is the root bark of the dicotyledonous perennial grass belonging to the family Leguminosae, order Rosales, used after drying. The root is usually harvested in the second autumn after seeding, but is also occasionally
} harvested in the first or third autumn. The *astragali radix* is known to contain more than 40 kinds of triterpene glycosides (saponins), polysaccharides such as astgaram I and II, flavonoids such as kaempferol and quercertin, more than 20 kinds of free amino acids, and more than 20 kinds of trace elements including iron and magnesium.

Known pharmacological activities of the *astragali radix* include enhancement of immunity, antiviral and antibacterial activities, promotion of nucleic acid synthesis in the liver and spleen, antioxidative activity, protection of the liver, and vasodilating and blood pressure-reducing activities. In the Oriental medicine, it is used to treat inflammation, fever, congestion, pain, infirmity or the like, especially to treat infirmity and cold sweat.

In the present disclosure, *astragali radix* extract exhibits the effect of promoting expression of PGC1-α, particularly in muscle cells. As a result, it promotes fatty acid oxidation by mitochondria and thus promotes production of ATP energy. Accordingly, it has an effect of promoting energy consumption and muscular metabolism. In addition, it may have an effect of increasing basal metabolic rate, reducing muscular damage, enhancing stamina, strengthening muscles, and relieving muscular pain.

In an exemplary embodiment of the present disclosure, the *astragali radix* extract comprises the extract of any part of astragalus, including leaves, stem and root. In another exemplary embodiment of the present disclosure, the *astragali radix* extract comprises the extract of the root of astragalus.

In an exemplary embodiment of the present disclosure, the *astragali radix* extract may be prepared by adding 10 volume equivalents of distilled water to *astragali radix*, extracting for about 3 hours in an extractor, filtered through Whatman No. 1 filter paper, and freeze drying at −70° C. However, any commonly employed extraction method may be used without being particularly limited thereto.

In an exemplary embodiment of the present disclosure, the *astragali radix* extract may be included in the composition in an amount of 1-100 wt % based on the total weight of the composition. In another exemplary embodiment of the present disclosure, the *astragali radix* extract may be included in an amount of 1-80 wt % based on the total weight of the composition. In another exemplary embodiment of the present disclosure, the *astragali radix* extract may be included in an amount of 10-60 wt % based on the total weight of the composition. When the *astragali radix* extract is included in an amount less than 1 wt %, the effect desired in the present disclosure may not be achieved sufficiently.

The present disclosure also provides a pharmaceutical composition which comprises the composition comprising the *astragali radix* extract. The pharmaceutical composition which comprises the *astragali radix* extract having the effect of improving energy consumption and muscular metabolism may also have an effect of improving energy consumption and muscular metabolism.

The pharmaceutical composition may further comprise a pharmaceutical adjuvant such as preservative, stabilizer, wetting agent, emulsifier, salt for osmotic control and/or buffer or other therapeutically useful substance, and may be formulated into various oral or parenteral administration forms according to methods known in the art.

Formulations for oral administration include, for example, tablet, pill, hard and soft capsule, liquid, suspension, emulsion, syrup, powder, dust, granule, pellet or the like. These formulations may comprise a surfactant, a diluent (for example, lactose, dextrose, sucrose, mannitol, sorbitol, cellulose or glycine), a lubricant (for example, silica, talc, stearic acid and its magnesium or calcium salt, or polyethylene glycol) and a binder (for example, magnesium aluminum silicate, starch paste, gelatin, tragacanth, methyl cellulose, sodium carboxymethyl cellulose or polyvinylpyrrolidone), in addition to the active ingredient. As occasion demands, it may also comprise a pharmaceutical additive such as a disintegrant, an absorbent, a colorant, a flavor, a sweetener or the like, for example, starch, agar, alginic acid or its sodium salt. A tablet may be prepared by the common mixing, granulation or coating method.

Formulations for parenteral administration include, for example, injection, medicinal drop, ointment, lotion, gel, cream, spray, suspension, emulsion, suppository or patch, but are not limited thereto.

The pharmaceutical composition according to the present disclosure may be administered orally or parenterally, for example, rectally, topically, transdermally, intravenously, intramuscularly, intraperitoneal or subcutaneously.

The administration dosage of the active ingredient will vary depending on the age, gender, body weight, particular disease or pathological condition to be treated, or severity of the disease or pathological condition of the subject, administration route and discretion of a diagnoser. Determination of the administration dosage considering these factors is in the level of those skilled in the art.

The present disclosure also provides a food composition which comprises the composition comprising the *astragali radix* extract. The food composition which comprises the *astragali radix* extract having the effect of improving energy consumption and muscular metabolism may also have an effect of improving energy consumption and muscular metabolism.

Formulations of the food composition include, for example, tablet, granule, drink, caramel, diet bar, tea bag or the like, but are not particularly limited thereto. The food composition may be prepared by those skilled in the art without special difficulty using the active ingredient and other ingredients commonly used in the art considering particular formulation type or purpose of use. A synergic effect may be achieved when the active ingredient is used in combination with other ingredients.

Determination of the administration dosage of the active ingredient is in the level of those skilled in the art. A daily dosage may vary depending on various factors such as the age or health condition of the subject, presence of complication(s), or the like.

MODE FOR INVENTION

Hereinafter, the present disclosure will be described in more detail through examples and experiments. The following examples and experiments are for illustrative purposes only and not intended to limit the scope of the present disclosure.

EXAMPLE

Preparation of *Astragali radix* Extract

*Astragali radix* harvested in Korea was purchased from a local market. The *astragali radix* was mixed with triply distilled water (1:10) and extracted for 3 hours in an extractor. After repeating this procedure 2 times, the resulting extract was filtered through filter paper. The filtrate was concentrated under reduced pressure using a rotary vacuum evaporator and freeze dried to obtain dry powder.

Test Example 1

Activation of APRDC PGC1-α Promoter

APRDC PGC1-α promoter was treated with the *astragali radix* extract and other substances known to activate PGC1-α promoter. APRDC PGC1-α promoter is a human liver cell line (KCTC 11218BP) which is a stable expression vector genetically fused PGC1-α with the luciferase gene.

First, APRDC PGC1-α promoter was treated for 24 hours with 200 μg/mL *astragali radix* extract prepared in the Example. Then, after washing 2 times with phosphate buffered saline (PBS), the activity of the reporter gene luciferase was measured using a luciferase assay kit (Steady Glo luciferase assay system, Promega, Cat No. E2520). The luciferase activity was measured by transferring the sample to a 96-well plate and measuring fluorescence emission using a luminometer. The same experiment was performed with dimethyl sulfoxide (DMSO) as negative control, *Puerariae flos, Citrus leiocarpa*, FMM, *Citrus erythrosa, Citrus poonensis, Citrus sphaerocarpa*, sinetrol, *Citrus tachibana*, licorice root, *Citrus grandis* and seminole. The result is shown in FIG. 1.

As seen from FIG. 1, the *astragali radix* extract exhibited stronger fluorescence not only than that of 200 μg/mL DMSO as the negative control but also that of other substances known to activate the PGC1-α promoter, meaning that the *astragali radix* extract has a very superior effect of activating the APRDC PGC1-α promoter. Thus, it was confirmed that the *astragali radix* extract has an excellent effect of promoting expression of PGC1-α.

Test Example 2

Promotion of Expression of PGC1-α Gene in Muscle Cells

In order to investigate whether the *astragali radix* extract actually has the effect of promoting the expression of the PGC1-α gene in muscle cells, the astragali radix extract was dissolved in DMSO and test was conducted as follows.

Immature C2C12 muscle cells were acquired from the American Type Culture Collection (ATCC, USA) and cultured in Dulbecco's modified Eagle's medium (DMEM; Gibco, USA) containing 10% fetal bovine serum (FBS; Gibco, USA) until 70% confluency in a 5% $CO_2$ incubator (while replacing the medium every other day). The cells were induced to differentiate into muscle cells by culturing in a medium containing 2% horse serum (HS; Gibco, USA). After culturing for 4 days in the medium containing 2% HS, the muscle cells were treated with 200 μg/mL *astragali radix* extract. A negative control group was treated with DMSO (1/1000 volume with respect to the medium). The treated cells were respectively cultured at 37° C. for 24 hours and, after washing 2 times with cold saline, RNA was extracted using a TRIzol agent (Invitrogen). Then, cDNA was synthesized using the extracted 1 μg/μL RNA and a reverse transcription PCR system (Promega, USA).

Expression level of PGC1-α was measured using the synthesized cDNA as well as a primer and a probe designed for PGC1-α (Applied Biosystems; PGC1-α, Mm00447181_ml, GAPDH, Mm99999915_q1). The PCR and analysis were performed using the Rotor-Gene 3000 system (Corbett Research, Sidney, Australia). The result is shown in FIG. 2.

As seen from FIG. 2, the *astragali radix* extract shows a very superior expression of PGC1-α as compared to the negative control group. Thus, it was confirmed that the *astragali radix* extract promotes the expression of PGC1-α in muscle cells.

Hereinafter, formulation examples of pharmaceutical and food compositions which comprise the composition comprising the *astragali radix* extract as an active ingredient will be described in more detail. The following formulation examples are for illustrative purposes only and not intended to limit the scope of the present disclosure.

Formulation Example 1

Preparation of Tablet

| | |
|---|---|
| Astragali radix extract | 50 mg |
| Corn starch | 100 mg |
| Lactose | 100 mg |
| Magnesium stearate | 2 mg |
| Vitamin C | 50 mg |

The above ingredients are mixed and prepared into a tablet according to a commonly employed method.

Formulation Example 2

Preparation of Capsule

| | |
|---|---|
| Astragali radix extract | 50 mg |
| Corn starch | 100 mg |
| Lactose | 100 mg |
| Magnesium stearate | 2 mg |
| Vitamin C | 50 mg |
| Serine | 50 mg |

The above ingredients are mixed and filled in a gelatin capsule according to a commonly employed method to prepare a capsule.

Formulation Example 3

Preparation of Liquid

| | |
|---|---|
| Astragali radix extract | 100 mg |
| Isomerized sugar | 10 g |
| Mannitol | 5 g |
| Vitamin C | 50 mg |
| Serine | 50 mg |
| Fat | adequate |
| Purified water | remainder |

According to a commonly employed method, the above ingredients are dissolved in purified water and mixed after adding an adequate amount of lemon flavor. Then, purified water is added to make 100 mL. The prepared liquid is filled in a brown bottle and sterilized.

Formulation Example 4

Preparation of Health Food

| | |
|---|---|
| Astragali radix extract | 1000 mg |
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate, monobasic | 15 mg |
| Calcium phosphate, dibasic | 55 mg |
| Potassium citrate | 90 mg |
| Calcium carbonate | 100 mg |
| Magnesium chloride | 24.8 mg |

Although the above-described composition of vitamin and mineral mixtures is given as a specific example adequate for a health food, it may also be altered otherwise. The above ingredients are mixed and prepared into a granule according to a commonly employed method to prepare a health food composition.

Formulation Example 5

Preparation of Drink

| | |
|---|---|
| Astragali radix extract | 1000 mg |
| Citric acid | 1000 mg |
| Oligosaccharide | 100 g |
| Plum concentrate | 2 g |
| Taurine | 1 g |
| Purified water | to make 1000 mL |

According to a commonly employed method, the above ingredients are mixed and stirred for about 1 hour while heating at 85° C. The resulting solution is filled in a sterilized 2-L container, sealed up, sterilized and stored in a refrigerator to be used to prepare a drink composition.

The invention claimed is:

1. A method for activating peroxisome proliferator-activated receptor gamma coactivator 1-alpha(PGC1-α) promoter, comprising:
    parenterally administering to a subject in need of increasing basal metabolic rate a composition comprising an active component and a pharmaceutically acceptable carrier,
    wherein the active component consists of an *astragali radix* powdered freeze-dried extract,
    wherein the *astragali radix* powdered freeze-dried extract content is comprised in an amount of 10-60 wt % based on the total weight of the composition,
    and
    wherein the composition promotes production of mitochondria in the subject,
    wherein the *astragali radix* powdered freeze-dried extract is prepared by mixing *astragali radix* with triply distilled water as a ratio of 1:10, extracting the mixture for 3 hours in an extractor and repeating the mixing and extracting 2 times, filtering the resulting extract through a filter paper, concentrating the filtrate under reduced pressure, and freeze-drying the concentrate to obtain dry powder of *astragali radix* extract.

2. The method according to claim 1, wherein parenteral administration comprises injection.

3. The method according to claim 1, wherein the pharmaceutically acceptable carrier comprises a diluent.

4. The method according to claim 3, wherein the diluent is lactose.

* * * * *